US012718141B2

(12) United States Patent
Harinen

(10) Patent No.: US 12,718,141 B2
(45) Date of Patent: Aug. 25, 2026

(54) SYSTEMS AND METHODS FOR PREDICTING THE EFFECT OF AN INTERVENTION VIA MACHINE LEARNING

(71) Applicant: Toyota Research Institute, Inc., Los Altos, CA (US)

(72) Inventor: Totte Harinen, Sunnyvale, CA (US)

(73) Assignee: Toyota Research Institute, Inc., Los Altos, CA (US)

( * ) Notice: Subject to any disclaimer, the term of this patent is extended or adjusted under 35 U.S.C. 154(b) by 1069 days.

(21) Appl. No.: 17/586,147

(22) Filed: Jan. 27, 2022

(65) Prior Publication Data

US 2023/0131677 A1 Apr. 27, 2023

Related U.S. Application Data

(60) Provisional application No. 63/270,326, filed on Oct. 21, 2021.

(51) Int. Cl.
*G06N 20/00* (2019.01)
*G16H 20/10* (2018.01)

(52) U.S. Cl.
CPC ............ *G06N 20/00* (2019.01); *G16H 20/10* (2018.01)

(58) Field of Classification Search
CPC ................................ G06N 20/00; G06N 3/08
See application file for complete search history.

(56) References Cited

U.S. PATENT DOCUMENTS

| | | | | |
|---|---|---|---|---|
| 11,468,364 | B2 * | 10/2022 | Shi | G06N 20/20 |
| 2020/0395129 | A1 | 12/2020 | Kalkstein et al. | |
| 2023/0074781 | A1 * | 3/2023 | Luo | C12Q 1/6886 |
| 2023/0075453 | A1 * | 3/2023 | Mitra | G06F 16/285 |
| 2023/0076243 | A1 * | 3/2023 | Watt | G06Q 40/08 |
| 2023/0230708 | A1 * | 7/2023 | Mahna | G16H 50/20 |

(Continued)

OTHER PUBLICATIONS

Chomboon, Kittipong; An Empirical Study of Distance Metrics for k-Nearest Neighbor Algorithm, 2015, 3rd International Conference on Industrial Application Engineering. pp. 280-285 (Year: 2015).*

(Continued)

*Primary Examiner* — Dylan C White
(74) *Attorney, Agent, or Firm* — Christopher G. Darrow; Darrow Mustafa PC

(57) ABSTRACT

Systems and methods described herein relate to predicting the effect of an intervention via machine learning. One embodiment divides a plurality of units into first and second intervention groups that receive first and second interventions, respectively; identifies, for each unit, k nearest-neighbor units in each of the first and second intervention groups; calculates, for each unit, an outcome under the first and second interventions as first and second weighted averages of the k nearest-neighbor units in the first and second intervention groups, respectively; calculates, for each unit, an intervention effect for that unit as the difference between the outcomes under the first and second interventions; generates a machine-learning-based regression model that models the intervention effects of the units as a function of a set of covariates; and outputs, using the machine-learning-based regression model, a predicted intervention effect for a unit that is outside the plurality of units.

18 Claims, 3 Drawing Sheets

(56) References Cited

U.S. PATENT DOCUMENTS

| | | | | |
|---|---|---|---|---|
| 2023/0352125 | A1* | 11/2023 | Fisher | G16H 10/60 |
| 2023/0401457 | A1* | 12/2023 | Sodhi | G06N 20/00 |
| 2024/0105298 | A1* | 3/2024 | Netzer | G16H 40/20 |
| 2024/0265301 | A1* | 8/2024 | Ogino | G06N 20/00 |
| 2025/0078965 | A1* | 3/2025 | Vanderbeek | G16H 50/50 |

OTHER PUBLICATIONS

P. Steiner and D. Cook, "Matching and Propensity Scores," The Oxford Handbook of Quantitative Methods vol. 1: Foundations, Oxford University Press, Inc., 2013, found at https://www.researchgate.net/file.PostFileLoader.html?id=5644cb985f7f71421f8b459f&assetKey=AS%3A295017840168964%401447349142456#page=256.

C. Heinrich et al., "A Primer for Applying Propensity-Score Matching: Impact-Evaluation Guidelines," Office of Strategic Planning and Development Effectiveness, Inter-American Development Bank, 2010, found at https://www.researchgate.net/profile/Carolyn-Heinrich/publication/235712818_A_Primer_for_Applying_Propensity-Score_Matching/links/57dd90b508aeea195938c939/A-Primer-for-Applying-Propensity-Score-Matching.pdf (.

S. Kuenzel, "Heterogeneous Treatment Effect Estimation Using Machine Learning," doctoral dissertation, University of California, Berkeley, 2019, found at https://www.pnas.org/content/pnas/116/10/4156.full.pdf.

J. Rubel et al., "Predicting Personalized Process-Outcome Associations in Psychotherapy Using Machine Learning Approaches—A Demonstration," Psychotherapy Research, 2019, found at https://psychotherapy.haifa.ac.il/images/Publications/073.pdf.

R. Bell and Y. Koren, "Improved Neighborhood-Based Collaborative Filtering," KDDCup '07, Aug. 12, 2007, San Jose, CA, ACM, found at http://citeseerx.ist.psu.edu/viewdoc/download?doi=10.1.1.443.300&rep=rep1&type=pdf.

Y. Xie et al., "Estimating Heterogeneous Treatment Effects with Observational Data," Social. Methdol., Aug. 2012, pp. 314-47, found at https://www.ncbi.nlm.nih.gov/pmc/articles/PMC3591476/pdf/nihms-341345.pdf.

S. Powers et al., "Some Methods for Heterogeneous Treatment Effect Estimation in High Dimensions," Stat. Med., May 2018, pp. 1767-1787, found at https://www.ncbi.nlm.nih.gov/pmc/articles/PMC5938172/pdf/nihms956481.pdf.

A. Caron et al., "Estimating Individual Treatment Effects Using Non-Parametric Regression Models: A Review," arXiv:2009.06472v4 [stat.ME], Apr. 25, 2021, found at https://arxiv.org/pdf/2009.06472.pdf.

S. Künzel et al., "Metalearners for Estimating Heterogeneous Treatment Effects Using Machine Learning," PNAS, Mar. 5, 2019, vol. 116, No. 10, pp. 4156-4165, found at https://www.proquest.com/openview/43c2b65d0c79743d752664e1f8b2a11f/1?pq-origsite=gscholar&cbl=51922&diss=y.

Eva Ascarza. \Retention futility: Targeting high-risk customers might be ineective. In: Journal of Marketing Research 55.1 (2018), pp. 80-98.

Huigang Chen et al. \Causalml: Python package for causal machine learning. In: arXiv preprint arXiv:2002.11631 (2020).

Pierre Gutierrez and Jean-Yves Gerardy. "Causal Inference and Uplift Modelling: A Review of the Literature". In: Proceedings of the 3rd International Conference on Predictive Applications and APIs. Ed. by Claire Hardgrove et al. vol. 67. Proceedings of Machine Learning Research. Microsoft NERD, Boston, USA: PMLR, 2017, pp. 1-13.

Behram Hansotia and Brad Rukstales. \Incremental value modeling. en. In: J. Interact. Mark. 16.3 (Jan. 2002), pp. 35-46.

Jeroen Hoogland et al. \A tutorial on individualized treatment effect prediction from randomized trials with a binary endpoint. In: Statistics in Medicine n/a.n/a (). doi: https://doi.org/10.1002/sim.9154. eprint: https://onlinelibrary.wiley.com/doi/pdf/10.1002/sim.9154. url: https://onlinelibrary.wiley.com/doi/abs/10.1002/sim.9154.

Adam Kapelner et al. "Evaluating the Effectiveness of Personalized Medicine With Software". en. In: Front Big Data 4 (May 2021), p. 572532.

Soren R. Kunzel et al. "Metalearners for estimating heterogeneous treatment effects using machine learning". en. In: Proc. Natl. Acad. Sci. U.S.A. 116.10 (Mar. 2019), pp. 4156-4165.

David Lewis. "Causation". In: Journal of Philosophy 70.17 (1973), pp. 556-567. doi: 10.2307/2025310.

Ang Li and Judea Pearl. "Unit selection based on counterfactual logic". In: Proceedings of the Twenty-Eighth International Joint Conference on Artificial Intelligence. Macao, China: International Joint Conferences on Artificial Intelligence Organization, Aug. 2019.

Christos Louizos et al. "Causal effect inference with deep latent-variable models". In: arXiv preprint arXiv: 1705.08821 (2017).

Peter Menzies and Helen Beebee. "Counterfactual Theories of Causation". In: The Stanford Encyclopedia of Philosophy. Ed. by Edward N. Zalta. Winter 2020. Metaphysics Research lab, Stanford University, 2020.

Xinkun Nie and Stefan Wager. Quasi-Oracle Estimation of Heterogeneous Treatment Effects. 2020. arXiv: 1712.04912.

Fabian Pedregosa et al. "Scikit-learn: Machine learning in Python." In: The Journal of Machine Learning Research 12 (2011), pp. 2825-2830.

Nicholas J. Radcliffe and Patrick D. Surry. "Real-world uplift modelling with significance-based uplift trees." In: White Paper TR-2011-1, Stochastic Solutions (2011), pp. 1-33.

Paul R. Rosenbaum and Donald B. Rubin. "The central role of the propensity score in observational studies for causal effects." In: Biometrika 70.1 (1983), pp. 41-55.

Donald B. Rubin. "Estimating causal effects of treatments in randomized and nonrandomized studies." In: Journal of educational Psychology 66.5 (1974), p. 688.

Piotr Rzepakowski and Szymon Jaroszewicz. "Decision trees for uplift modeling with single and multiple treatments." In: Knowledge and Information Systems 32.2 (2012), pp. 303-327.

Vasilis Syrgkanis et al. "Causal Inference and Machine Learning in Practice with EconML and CausalML: Industrial Use Cases at Microsoft, TripAdvisor, Uber." In: Proceedings of the 27th ACM SIGKDD Conference on Knowledge Discovery amp; Data Mining. KDD '21. Virtual Event, Singapore: Association for Computing Machinery, 2021, pp. 4072-7043.

Stefan Wager and Susan Athey. "Estimation and Inference of Heterogeneous Treatment Effects using Random Forests." In: J. Am. Stat. Assoc. 113.523 (Jul. 2018), pp. 1228-1242.

Yan Zhao, Xiao Fang, and David Simchi-Levi "Uplift Modeling with Multiple Treatments and General Response Types." In: Proceedings of the 2017 SIAM International Conference on Data Mining (SDM). Proceedings. Society for Industrial and Applied Mathematics, Jun. 2017, pp. 588-596.

Zhenyu Zhao and Totte Harinen. "Uplift Modeling for Multiple Treatments with Cost Optimization." In: 2019 IEEE International Conference on Data Science and Advanced Analytics (DSAA). ieeexplore.ieee.org, Oct. 2019, pp. 422-431.

* cited by examiner

Network
250
Other Network Nodes
255

Intervention-Effect Prediction System 100
Database 235
Nearest Neighbors
240
Intervention Effects
130
Predicted Intervention Effects
135
Designated Interventions
145
Covariates
120
Model Data
245
Intervention Outcome Data
125
Processor(s)
205
Memory 210
Group Identification Module
215
Matching Module
220
Regression Module
225
Prediction Module
230

SYSTEMS AND METHODS FOR PREDICTING THE EFFECT OF AN INTERVENTION VIA MACHINE LEARNING

CROSS-REFERENCE TO RELATED APPLICATION

This application claims the benefit of U.S. Provisional Patent Application No. 63/270,326, "Systems and Methods for Learning Heterogeneous Effects Within Different Groups," filed on Oct. 21, 2021, which is incorporated by reference herein in its entirety.

TECHNICAL FIELD

The subject matter described herein relates in general to machine learning and, more specifically, to systems and methods for predicting the effect of an intervention via machine learning.

BACKGROUND

In a variety of fields, including business, policy, and medicine, systems are designed that estimate how the effects of an intervention (e.g., a treatment, in the medical context) vary among individuals and groups. This variation in the effects of an intervention is sometimes referred to in the literature as "treatment-effect heterogeneity." For example, technology companies and marketers are interested in knowing which segments of customers value a certain product feature or which customers will respond positively or negatively to a marketing message. Medical researchers might want to understand whether a particular drug will have negative side effects for certain individuals or groups. Recently, there has been a significant increase in the number of machine-learning-based approaches to learning treatment-effect heterogeneity.

SUMMARY

An example of a system for predicting an effect of an intervention via machine learning is presented herein. The system comprises one or more processors and a memory communicably coupled to the one or more processors. The memory stores a group identification module including instructions that when executed by the one or more processors cause the one or more processors to divide a plurality of units into a first intervention group and a second intervention group. The units in the first intervention group receive a first intervention and the units in the second intervention group receive a second intervention. The memory also stores a matching module including instructions that when executed by the one or more processors cause the one or more processors to identify, for each unit in the plurality of units, k nearest-neighbor units in the first intervention group and k nearest-neighbor units in the second intervention group, wherein k is a natural number. The matching module also includes instructions that when executed by the one or more processors cause the one or more processors to calculate, for each unit in the plurality of units, an outcome under the first intervention as a first weighted average of the k nearest-neighbor units in the first intervention group and an outcome under the second intervention as a second weighted average of the k nearest-neighbor units in the second intervention group. The matching module also includes instructions that when executed by the one or more processors cause the one or more processors to calculate, for each unit in the plurality of units, an intervention effect for that unit as a difference between the outcome under the first intervention and the outcome under the second intervention. The memory also stores a regression module including instructions that when executed by the one or more processors cause the one or more processors to generate a machine-learning-based regression model that models the intervention effects of the units in the plurality of units as a function of a set of covariates associated with the units in the plurality of units. The memory also stores a prediction module including instructions that when executed by the one or more processors cause the one or more processors to output, using the machine-learning-based regression model, a predicted intervention effect for a unit that is outside the plurality of units.

Another embodiment is a non-transitory computer-readable medium for predicting an effect of an intervention via machine learning and storing instructions that when executed by one or more processors cause the one or more processors to divide a plurality of units into a first intervention group and a second intervention group. The units in the first intervention group receive a first intervention and the units in the second intervention group receive a second intervention. The instructions also cause the one or more processors to identify, for each unit in the plurality of units, k nearest-neighbor units in the first intervention group and k nearest-neighbor units in the second intervention group, wherein k is a natural number. The instructions also cause the one or more processors to calculate, for each unit in the plurality of units, an outcome under the first intervention as a first weighted average of the k nearest-neighbor units in the first intervention group and an outcome under the second intervention as a second weighted average of the k nearest-neighbor units in the second intervention group. The instructions also cause the one or more processors to calculate, for each unit in the plurality of units, an intervention effect for that unit as a difference between the outcome under the first intervention and the outcome under the second intervention. The instructions also cause the one or more processors to generate a machine-learning-based regression model that models the intervention effects of the units in the plurality of units as a function of a set of covariates associated with the units in the plurality of units. The instructions also cause the one or more processors to output a predicted intervention effect for a unit that is outside the plurality of units using the machine-learning-based regression model.

Another embodiment is a method of predicting an effect of an intervention via machine learning, the method comprising dividing a plurality of units into a first intervention group and a second intervention group. The units in the first intervention group receive a first intervention and the units in the second intervention group receive a second intervention. The method also includes identifying, for each unit in the plurality of units, k nearest-neighbor units in the first intervention group and k nearest-neighbor units in the second intervention group, wherein k is a natural number. The method also includes calculating, for each unit in the plurality of units, an outcome under the first intervention as a first weighted average of the k nearest-neighbor units in the first intervention group and an outcome under the second intervention as a second weighted average of the k nearest-neighbor units in the second intervention group. The method also includes calculating, for each unit in the plurality of units, an intervention effect for that unit as a difference between the outcome under the first intervention and the outcome under the second intervention. The method also includes generating a machine-learning-based regression model that models the intervention effects of the units in the plurality of units as a function of a set of covariates associated with the units in the plurality of units. The method also includes outputting, using the machine-learning-based regression model, a predicted intervention effect for a unit that is outside the plurality of units.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

To facilitate understanding, identical reference numerals have been used, wherever possible, to designate identical elements that are common to the figures. Additionally, elements of one or more embodiments may be advantageously adapted for utilization in other embodiments described herein.

DETAILED DESCRIPTION

Figure 1:
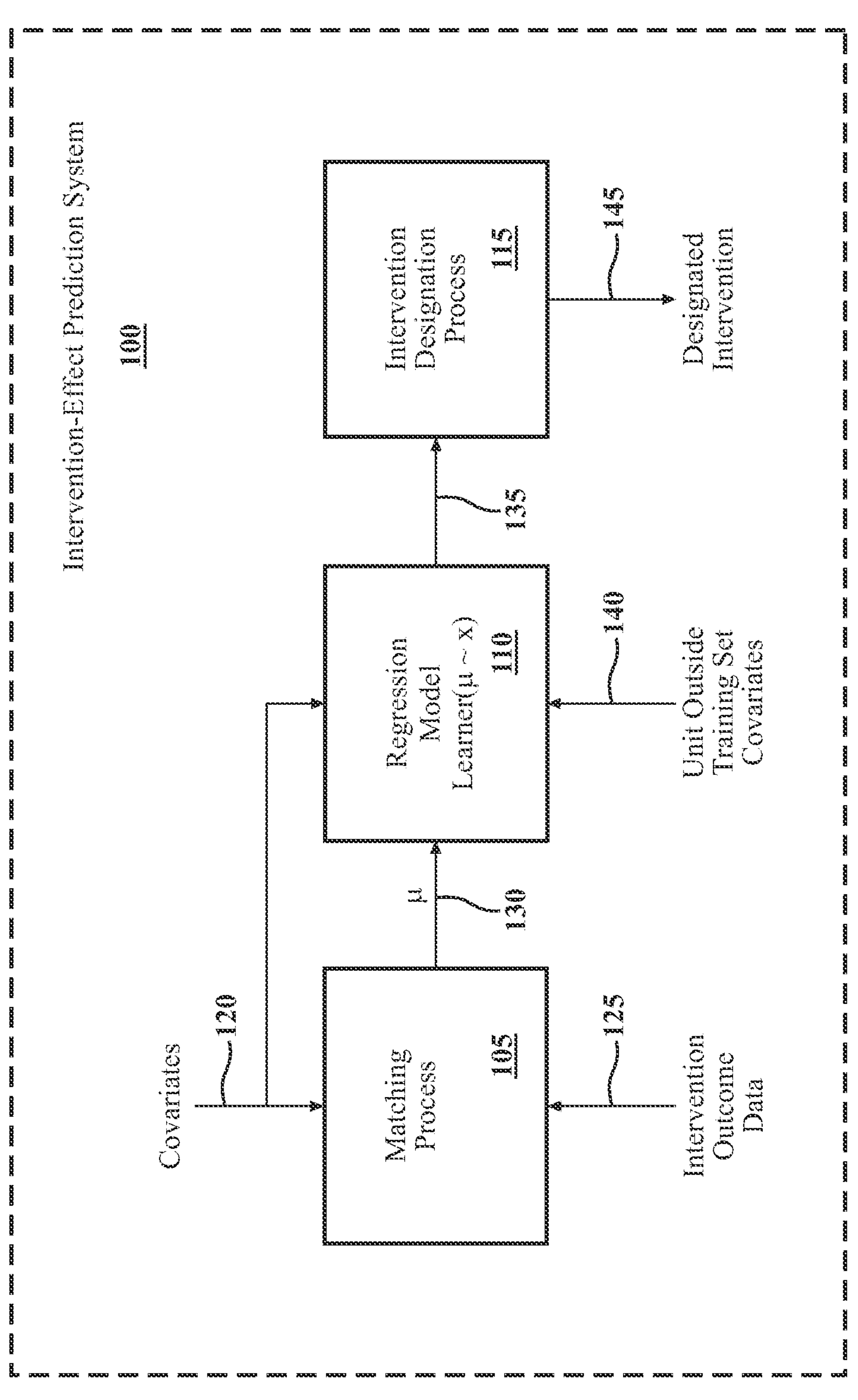
FIG. 1 is a functional block diagram of an intervention-effect prediction system, in accordance with an illustrative embodiment of the invention.

Various embodiments described herein improve on conventional machine-learning-based systems for learning treatment-effect heterogeneity by drawing inspiration from counterfactual theories of causation and employing nearest-neighbor matching. Because these embodiments are not tied to any specific machine learning algorithm, they may be categorized as "meta-learners." A meta-learner has the advantage of not requiring that the loss function of traditional machine-learning algorithms be modified.

Before proceeding with a description of these various embodiments, certain terms will first be defined and explained. Herein, an "intervention" is an action performed on an object or a condition or set of conditions to which the object is exposed or subjected. Some examples of an "intervention" include, without limitation, a marketing message or advertisement, exposure to a product feature or a change in a product feature relative to the status quo, a physical manipulation (e.g., stretching, bending, heating, cooling, painting, etc.), an electromagnetic manipulation (e.g., subjecting the object to an electric field, a magnetic field, and/or light), and a medical treatment (e.g., a medication or vaccine). A "unit" is the object or recipient of an intervention. Like the term "intervention," the term "unit" is quite broad, encompassing, without limitation, individual human beings, households, groups of human beings other than households, autonomous machines (e.g., an autonomous automobile or other autonomously moving robot), and inanimate objects (non-living objects that are not capable of moving on their own). For example, in one embodiment, the units might be individual people (e.g., consumers) or households to whom a particular marketing message is or is not communicated. In a different embodiment, the units might be electric bicycles that are distributed throughout a city for transportation. In yet another embodiment, the units might be individual people participating in a randomized trial of a new drug.

In various embodiments, once a machine-learning-based regression model has been trained on a training dataset using the techniques described herein, the trained machine-learning-based regression model can predict the effect of an intervention (the "intervention effect") on a unit that was not in the original training dataset. Such a prediction can support decision making such as whether to subject that unit to a particular intervention or to a different intervention to achieve a predetermined objective.

More specifically, in various embodiments of an intervention-effect prediction system, a plurality of units are divided into a first intervention group and a second intervention group, the first intervention group receiving a first intervention, the second intervention group receiving a second intervention. In some embodiments, the first and second interventions are two different interventions (e.g., different locations for a virtual button in a software app or an experimental drug vs. a placebo in a randomized medical trial). In other embodiments, the first intervention is an actual intervention of some kind, and the second intervention is a "null intervention" (i.e., the units in the second intervention group simply do not receive the first intervention that the units in the first intervention group receive). In such an embodiment, the second intervention group is what is commonly referred to as a "control group" in a randomized experiment or trial. Throughout this description, the designations "first" or "second" with respect to interventions or intervention groups is arbitrary.

Using nearest-neighbor matching, the system calculates, for each unit, an outcome under the first and second interventions as first and second weighted averages of k nearest-neighbor units in the first and second intervention groups, respectively. The system then calculates the intervention effect for each unit by subtracting the second weighted average for that unit from the first weighted average for that unit. This per-unit intervention effect becomes the dependent variable of a machine-learning-based regression model that learns to model the intervention effects of the units in the plurality of units as a function of a set of covariates that are associated with the units in the plurality of units. In other words, once the intervention effect has been estimated for each unit, it is possible to train a regression model on the relationship between the intervention effect and the covariates. The plurality of units discussed above are thus the training dataset for the machine-learning-based regression model. Once we have estimated the treatment effects for each unit using the approach discussed above, we can train any regression model on the relationship between the treatment effect and the covariates. The purpose of this step is to enable prediction to unseen samples, which has been a traditional concern for treatment effect heterogeneity learners. Unlike other state of the art meta-learners, the R-Learner and the X-Learner, the N-Learner trains a single base-learner directly on estimated treatment effects.

Consequently, giving an interpretation for the N-Learner reduces to the problem of giving an interpretation for the base-learner. This, along with the strong performance we saw in the experiments, may make the N-Learner a particularly appealing algorithm for practical applications. Depending on the embodiment, the machine-learning-based regression model can include one or more of a neural network, a linear regression model, and a decision-tree-based regression model. Examples of a decision-tree-based regression model include, without limitation, a decision-tree model, a random forest model, and a gradient-boosting model.

Once the machine-learning-based regression model has been trained, the system can output, using the machine-learning-based regression model, a predicted intervention effect for a unit that is outside the original plurality of units (i.e., outside the training dataset). In some embodiments, the system uses this predicted intervention effect to designate either the first intervention or the second intervention for the unit that is outside the plurality of units. That is, the system decides which of the two interventions should be applied to the unit that is outside the original plurality of units.

In some embodiments, the setting or context for an intervention-effect prediction system is a randomized experiment (i.e., the units in the first and second intervention groups are selected randomly or pseudorandomly). In other embodiments, the selection of the first and second intervention groups can be somewhat biased without seriously degrading the system's performance. This is one of the advantages of the various embodiments disclosed herein.

Referring to FIG. 1, it is a functional block diagram of an intervention-effect prediction system 100, in accordance with an illustrative embodiment of the invention. In the discussion of FIG. 1 that follows, certain assumptions apply. First, it is assumed that an experiment (in some embodiments, a randomized experiment) has been designed and that a plurality of units have been selected for the experiment and divided into two mutually exclusive groups, a first intervention group and a second intervention group. It is also assumed that the first intervention has been administered or applied to the units in the first intervention group and that the second intervention has been administered or applied to the units in the second intervention group. Recall that, in some embodiments, the second intervention is a null intervention and that the second intervention group is a control group. It is further assumed that data regarding the effects on the individual units in the first and second intervention groups as a result of the first and second interventions (intervention outcome data), respectively, has been collected and used, in conjunction with a set of covariates, to train a machine-learning-based regression model, as discussed above.

Part of the assumed precursor experimental design is the selection of a set of covariates associated with the units in the plurality of units. These covariates include information about each of the individual units in the plurality of units. For example, if the units are individual human beings, the covariates could include information such as gender, age, residential address, occupation, health history, etc. If the units are households, the covariates could include information such as household income, number of occupants, family relationships, etc. If the units are automobiles, the covariates could include information such as make, model year, color, installed optional accessories, mileage, etc. During the training of the machine-learning-based regression model, the regression model learns how to model the intervention effects of the units in the plurality of units as a function of the set of covariates associated with the units in the plurality of units, as discussed above. In some embodiments, the covariates associated with a given unit in the plurality of units is modeled mathematically as a vector, and the covariates associated with the units in the plurality of units are collectively modeled mathematically as a matrix X.

Returning to FIG. 1, intervention-effect prediction system 100 includes three primary functional blocks, matching process 105, regression model 110, and intervention designation process 115. The covariates 120 discussed above and the intervention outcome data 125 (the effects of the interventions on the individual units) are input to the matching process 105. The matching process 105 outputs, for each unit in the plurality of units, an intervention effect 130, as defined mathematically below. These intervention effects 130, along with the covariates 120, are input to the regression model 110 during the training of regression model 110.

Once regression model 110 has been trained, covariates (140) of a unit outside the training set can be input to regression model 110 to produce a predicted intervention effect 135 for the unit outside the training set. Based, at least in part, on the predicted intervention effect 135, intervention designation process 115 outputs a designated intervention 145 (either the first or second intervention) for the unit outside the training set. For example, intervention designation process 115 might select the first intervention (e.g., a particular policy or marketing message concerning climate change) for the unit (an individual person) outside the training set based, at least in part, on a positive/favorable predicted intervention effect 135 for the first intervention. The same is true for the second intervention (in this example, it is assumed that the first and second interventions are both actual interventions—that neither is a null intervention).

FIG. 1 provides a high-level functional overview of one embodiment of an intervention-effect prediction system 100. Additional details are provided below in connection with the illustrative implementation framework shown in FIG. 2.

Figure 2:
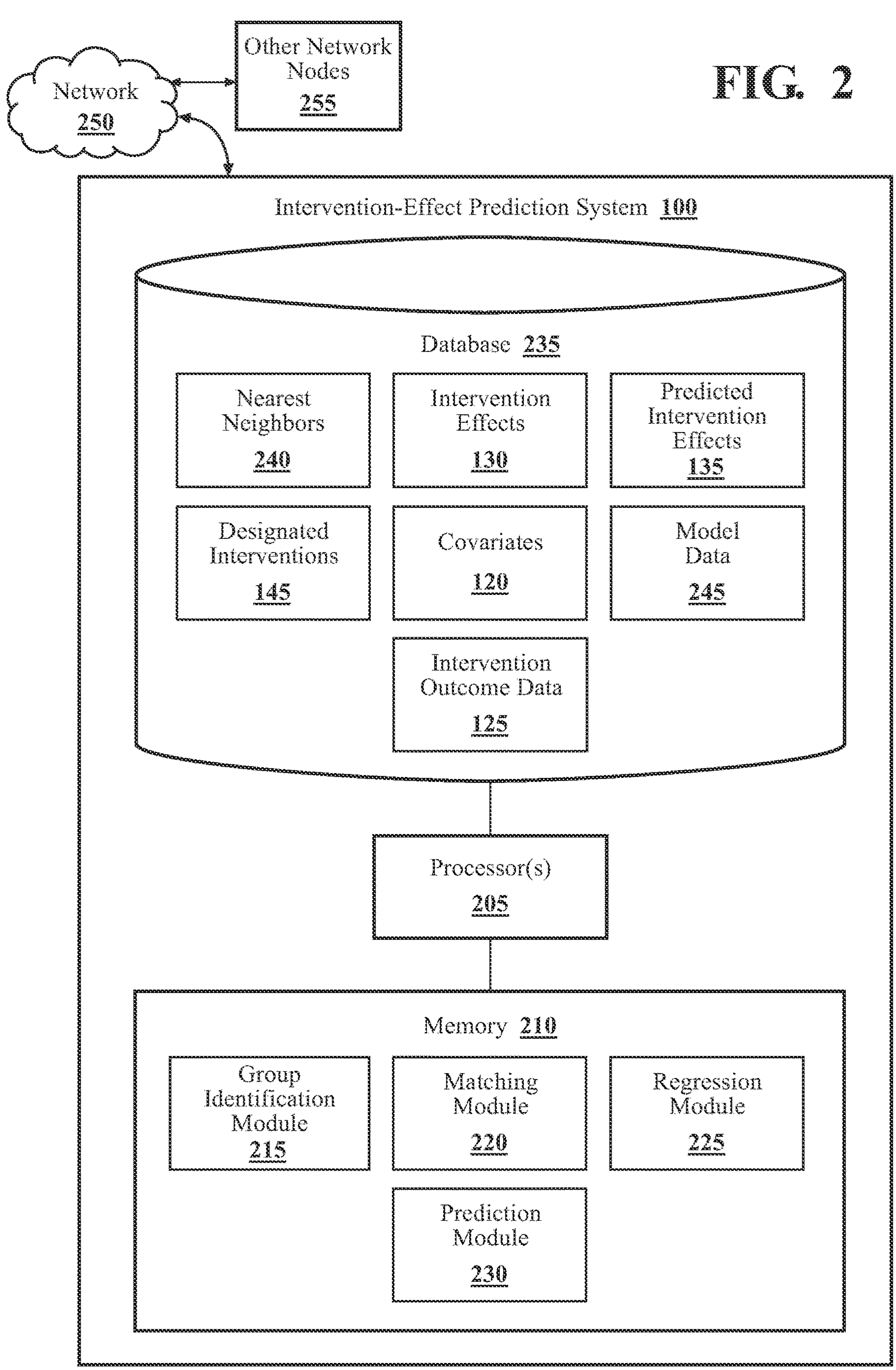
FIG. 2 is another block diagram of an intervention-effect prediction system, in accordance with an illustrative embodiment of the invention.

FIG. 2 is another block diagram of the intervention-effect prediction system 100 illustrated in FIG. 1, in accordance with an illustrative embodiment of the invention. FIG. 2 shows one possible implementation of intervention-effect prediction system 100. In some embodiments, intervention-effect prediction system 100 is implemented in a server computer. In other embodiments, intervention-effect prediction system 100 is implemented in a different type of computing system. In FIG. 2, intervention-effect prediction system 100 is shown as including one or more processors 205. Intervention-effect prediction system 100 also includes a memory 210 communicably coupled to the one or more processors 205. The memory 210 stores a group identification module 215, a matching module 220, a regression module 225, and a prediction module 230. The memory 210 is a random-access memory (RAM), read-only memory (ROM), a hard-disk drive, a flash memory, or other suitable memory for storing the modules 215, 220, 225, and 230. The modules 215, 220, 225, and 230 are, for example, computer-readable instructions that when executed by the one or more processors 205, cause the one or more processors 205 to perform the various functions disclosed herein.

In connection with its tasks, intervention-effect prediction system 100 can store various kinds of data in a database 235. For example, in the embodiment shown in FIG. 2, intervention-effect prediction system 100 stores, in database 235, covariates 120, intervention outcome data 125, intervention effects 130, predicted intervention effects 135, designated interventions 145, nearest neighbors 240, and model data 245. Model data 245 can include hyperparameters, weights, the results of intermediate calculations, and other data used in connection with training and, once trained, using regression model 110. Though not shown in FIG. 2, database 235 can also store the covariates 140 associated with one or more units that are not in the training dataset (not in the plurality of units discussed above).

As shown in FIG. 2, intervention-effect prediction system 100 can communicate with other network nodes 255 (e.g., other servers, client computers, mobile devices, etc.) via a network 250. In some embodiments, network 250 includes the Internet. Network 250 can include wired communication technologies such as Ethernet, as well as any of a variety of wireless communication technologies such as LTE, 5G, WiFi, and Bluetooth.

Group identification module 215 generally includes instructions that when executed by the one or more processors 205 cause the one or more processors 205 to divide a plurality of units into a first intervention group and a second intervention group. For example, group identification module 215 can process a database containing data (e.g., identity and associated covariates 120) concerning the units in the plurality of units to divide the plurality of units into the first and second intervention groups. In some embodiments, group identification module 215 randomly or pseudo-randomly assigns units in the plurality of units to the first and second intervention groups.

As discussed above, the units in the first intervention group receive a first intervention, and the units in the second intervention group receive a second intervention. As also discussed above, in some embodiments, the first and second interventions are two different interventions. In other embodiments, the first intervention is an actual intervention of some kind, and the second intervention is a "null intervention" (i.e., the units in the second intervention group simply do not receive the first intervention that the units in the first intervention group receive). In such an embodiment, the second intervention group is what is commonly referred to as a "control group" in a randomized experiment or trial. As also discussed above, in some embodiments, the setting or context for an intervention-effect prediction system is a randomized experiment. In other embodiments, the selection of the first and second intervention groups can be somewhat biased without seriously degrading the system's performance. This is one of the advantages of the approach described herein.

Matching module 220 generally includes instructions that when executed by the one or more processors 205 cause the one or more processors 205 to identify, for each unit in the plurality of units, k nearest-neighbor units in the first intervention group and k nearest-neighbor units in the second intervention group (240), wherein k is a natural number. The term "nearest neighbors" refers to units whose covariates, as a whole, are closest to those of the particular unit in question, according to a predetermined distance measure. In some embodiments, the predetermined distance measure is Euclidean distance (e.g., averaged over a plurality of covariates). In other words, in those embodiments, the matching module 220 identifies, for each unit in the plurality of units, the k nearest-neighbor units in the first intervention group and the k nearest-neighbor units in the second intervention group based on Euclidean distance with respect to the set of covariates associated with the units. In other embodiments, a distance measure other than Euclidean distance can be used.

Identifying the nearest neighbors 240 in each of the first and second intervention groups can be stated more formally as follows. Let $u_i$ denote the units in the plurality of units discussed above, $T \in \{0,1\}$ denote a binary intervention assignment for each unit $u_i$, $S_1=\{i:T_i=1\}$ denote the first intervention group, and $S_0=\{i:T_i=0\}$ denote the second intervention group. Matching module 220, for each unit $u_i$, finds the k nearest neighbors in each of $S_1=\{i:T_i=1\}$ and $S_0=\{i:T_i=0\}$. These k nearest neighbors 240 in the first and second intervention groups can be denoted, respectively, as $$S_1^{k_i}$$

and $$S_0^{k_i}.$$

Matching module 220 also includes instructions that when executed by the one or more processors 205 cause the one or more processors 205 to calculate, for each unit $u_i$ in the plurality of units, an outcome under the first intervention as a first weighted average of the k nearest-neighbor units in the first intervention group and an outcome under the second intervention as a second weighted average of the k nearest-neighbor units in the second intervention group. Mathematically stated, for each unit $u_i$, matching module 220 calculates the outcome under the first intervention as a first weighted average of the k nearest neighbors as follows:

$$Y_i(1) = \frac{\sum_{u_j \in s_1^{k_i}} Y_j d_j}{\sum_{u_j \in s_1^{k_i}} d_j},$$

where $d_j$ corresponds to the distance of the j-th unit from the unit $u_i$. Matching module 220 calculates, for each unit $u_i$, the outcome under the second intervention (in some embodiments, the control condition), $Y_i(0)$, in the same manner as above, except observations in $$S_0^{k_i}$$

are used.

Matching module 220 also includes instructions that when executed by the one or more processors 205 cause the one or more processors 205 to calculate, for each unit $u_i$ in the plurality of units, an intervention effect $\mu_i$ (130) for that unit as the difference between the outcome under the first intervention and the outcome under the second intervention, as defined above. This can be stated mathematically as $\mu_i=Y_i(1)-Y_i(0)$.

Regression module 225 generally includes instructions that when executed by the one or more processors 205 cause the one or more processors 205 to generate a machine-learning-based regression model 110 that models the intervention effects 130 of the units $u_i$ in the plurality of units as a function of a set of covariates X (120) associated with the units in the plurality of units. Let learner denote any regression model. Then, stated mathematically, learner($\mu \sim X$). As discussed above, depending on the embodiment, regression model 110 can include one or more of a neural network, a linear regression model, and a decision-tree-based regression model. As discussed above, the plurality of units $u_i$ and their associated covariates 120 and intervention effects 130 serve as the training dataset for the regression model 110.

Prediction module 230 generally includes instructions that when executed by the one or more processors 205 cause the one or more processors 205 to output, using the machinelearning-based regression model 110, a predicted intervention effect 135 for a unit that is outside the plurality of units. As discussed above, such a prediction can support decision making such as whether to subject that unit to a particular intervention (e.g., the first intervention) or to a different intervention (e.g., the second intervention or some other intervention). Such a prediction can have value in diverse fields, including policy, business, and medicine to support effective decision making. In some embodiments, prediction module 230 includes further instructions that when executed by the one or more processors 205 cause the one or more processors 205 to designate, for the unit that is outside the plurality of units, either the first intervention or the second intervention based, at least in part, on the predicted intervention effect 135. That is, prediction module 230 decides which of the two interventions should be applied to the unit that is outside the plurality of units. Recall from the discussion above that, in some embodiments, both the first and second interventions are actual interventions rather than the second intervention being a null intervention. Therefore, in those embodiments, prediction module 230 selects, for the unit outside the plurality of units, which of two different interventions is to be applied to the unit outside the plurality of units.

Figure 3:
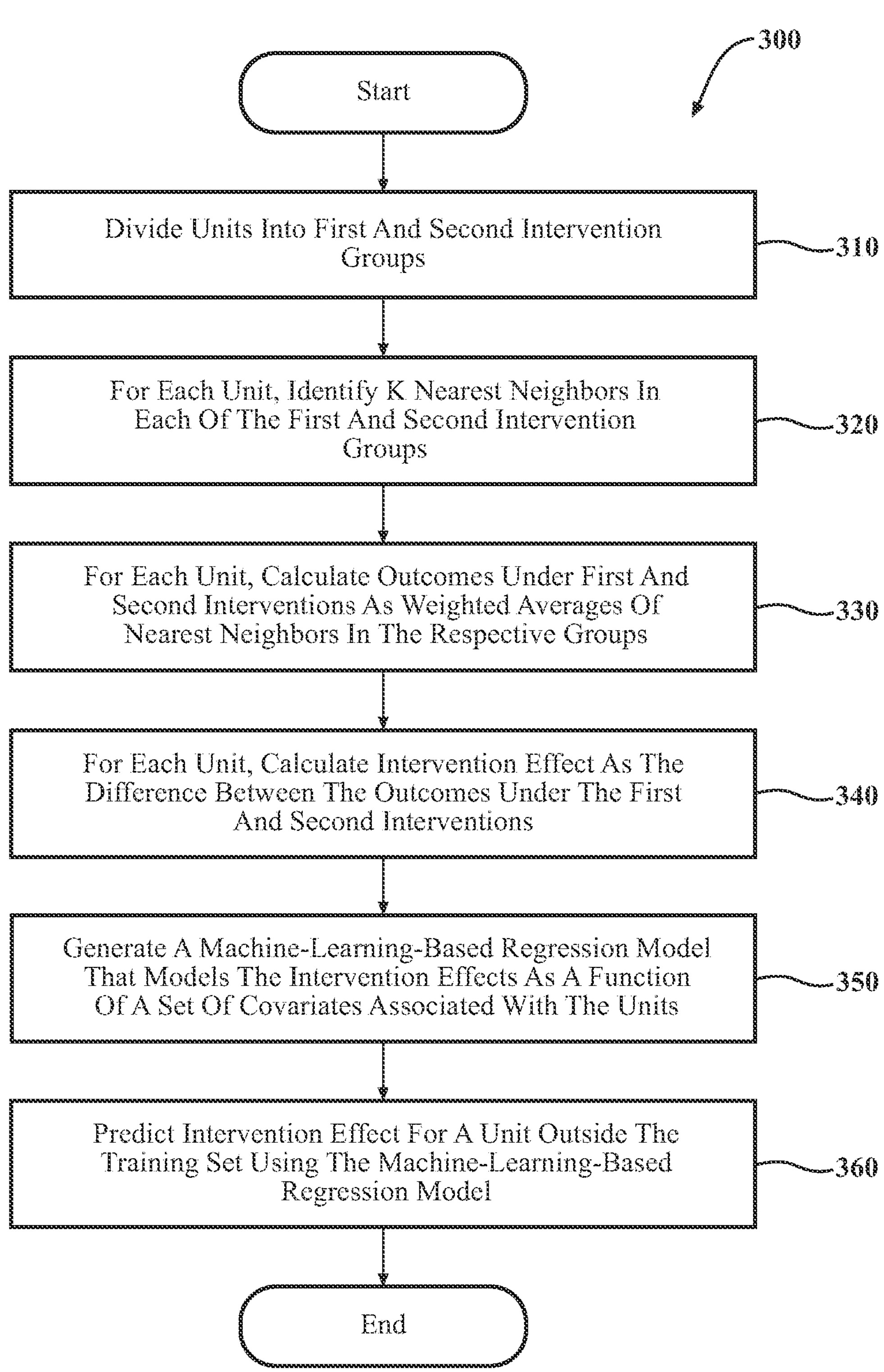
FIG. 3 is a flowchart of a method of predicting the effect of an intervention via machine learning, in accordance with an illustrative embodiment of the invention.

FIG. 3 is a flowchart of a method 300 of predicting the effect of an intervention via machine learning, in accordance with an illustrative embodiment of the invention. Method 300 will be discussed from the perspective of intervention-effect prediction system 100 in FIGS. 1 and 2. While method 300 is discussed in combination with intervention-effect prediction system 100, it should be appreciated that method 300 is not limited to being implemented within intervention-effect prediction system 100, but intervention-effect prediction system 100 is instead one example of a system that may implement method 300.

At block 310, group identification module 215 divides a plurality of units into a first intervention group and a second intervention group, wherein the units in the first intervention group receive a first intervention and the units in the second intervention group receive a second intervention. As discussed above, in some embodiments, group identification module 215 randomly or pseudorandomly assigns units in the plurality of units to the first and second intervention groups. As also discussed above, in some embodiments, the first and second interventions are two different interventions (e.g., different locations for an icon in a software app or an experimental drug vs. a placebo in a randomized medical trial). In other embodiments, the first intervention is an actual intervention of some kind, and the second intervention is a "null intervention" (i.e., the units in the second intervention group simply do not receive the first intervention that the units in the first intervention group receive). In such an embodiment, the second intervention group is what is commonly referred to as a "control group" in a randomized experiment or trial.

At block 320, matching module 220 identifies, for each unit in the plurality of units, k nearest-neighbor units in the first intervention group and k nearest-neighbor units in the second intervention group (240), wherein k is a natural number. As discussed above, the term "nearest neighbors" refers to units whose covariates, as a whole, are closest to those of the particular unit in question, according to a predetermined distance measure. In some embodiments, the predetermined distance measure is Euclidean distance (e.g., averaged over a plurality of covariates). In other words, in those embodiments, the matching module 220 identifies, for each unit in the plurality of units, the k nearest-neighbor units in the first intervention group and the k nearest-neighbor units in the second intervention group based on Euclidean distance with respect to the set of covariates associated with the units. A more formal mathematical statement of the actions performed at block 320 is presented above.

At block 330, matching module 220 calculates, for each unit in the plurality of units, an outcome under the first intervention as a first weighted average of the k nearest-neighbor units in the first intervention group and an outcome under the second intervention as a second weighted average of the k nearest-neighbor units in the second intervention group. A mathematical definition of the first and second weighted averages, in one embodiment, is provided above.

At block 340, matching module 220 calculates, for each unit in the plurality of units, an intervention effect 130 for that unit as a difference between the outcome under the first intervention and the outcome under the second intervention. The intervention effect 130 for a given unit is also defined mathematically above.

At block 350, regression module 225 generates a machine-learning-based regression model 110 that models the intervention effects 130 of the units in the plurality of units as a function of a set of covariates 120 associated with the units in the plurality of units. As discussed above, depending on the embodiment, regression model 110 can include one or more of a neural network, a linear regression model, and a decision-tree-based regression model. As also discussed above, the plurality of units and their associated covariates 120 and intervention effects 130 serve as the training dataset for the regression model 110.

At block 360, prediction module 230 outputs, using the trained machine-learning-based regression model 110, a predicted intervention effect 135 for a unit that is outside the plurality of units (i.e., for a unit that was not in the training dataset used to train the regression model 110). As discussed above, such a prediction can support decision making such as whether to subject that unit to a particular intervention (e.g., the first intervention) or to a different intervention (e.g., the second intervention or some other intervention).

In some embodiments, method 300 includes additional actions that are not shown in FIG. 3. For example, in some embodiments, prediction module 230 designates, for the unit that is outside the plurality of units, either the first intervention or the second intervention based, at least in part, on the predicted intervention effect 135. That is, prediction module 230 decides which of the two interventions should be applied to the unit that is outside the plurality of units. Recall from the discussion above that, in some embodiments, both the first and second interventions are actual interventions rather than the second intervention being a null intervention. Therefore, in those embodiments, prediction module 230 selects, for the unit outside the plurality of units, which of two different interventions is to be applied to the unit outside the plurality of units.

The actions performed in method 300, in one embodiment, are summarized below in the following listing for Algorithm 1 (in this listing, the term "treatment" is synonymous with "intervention," as defined above):

Algorithm 1 N-Learner procedure N-Learner(
X: covariates
T: binary treatment assignment $\in \{0,1\}$
Y: outcome of interest
learner: any regression model)

1. For each unit $u_i$, find the k nearest neighbors in $S_1 = \{i : T_i = 1\}$ and $S_0 = \{i : T_i = 0\}$.

Denote these $k$ nearest neighbors as $S_1^{k_i}$ and $S_0^{k_i}$, respectively.

2. For each unit $u_i$, calculate the outcome under treatment condition as the weighted average of the k nearest neighbors:

$$Y_i(1) = \frac{\Sigma_{u_j \in S_1^{k_i}} Y_j d_j}{\Sigma_{u_j \in S_1^{k_i}} d_j},$$

where $d_j$ corresponds to the distance of the j-th unit from the unit $u_i$. Calculate the outcome under the control condition, $Y_i(0)$, in the same way, except for using observations in $S_0^{k_i}$.

3. Calculate the treatment effect for each unit as the difference between the two outcomes:
$$\mu_i = Y_i(1) - Y_i(0).$$
4. Model the vector of estimated treatment effects as a function of the covariates:
$$\text{learner } (\mu \sim X).$$

As discussed above, the techniques for learning and applying intervention-effect heterogeneity (treatment-effect heterogeneity) described herein have application in a wide variety of fields and situations. For example, in one embodiment, intervention-effect prediction system 100 is used to predict the effect, on an individual person, of a marketing message concerning climate change. In another embodiment, the application is predicting the effect of an advertisement on a particular consumer. In another embodiment, a software developer might want to test the effect of changing the location of a virtual button in an app. Consider a group of 100 users. Some subset (e.g., 10) of those users can be randomly selected, and those users get a version of the app in which the button in question is moved to a new location. That group is the first intervention group. The second intervention group, the control group in this embodiment, is the remaining users, who use a version of the app in which the virtual button remains in the original location (the status quo). Such an experimental design can be mapped to the N-Learner algorithm (Algorithm 1) described above to predict the effect of the new button location on a specific user who was not in the original pool of 100 users selected as the training set. In this example, the outcome measured could be the extent to which the user "engages" with the button (how frequently the user actuates it, the user's dwell time on the associated feature, etc.). In a variation of this embodiment, the first intervention is to move the button to a first new location relative to the status quo, and the second intervention is to move the button to a second new location relative to the status quo. Such an application illustrates the flexibility of the above N-Learner algorithm.

In another embodiment, the units are shareable bicycles in a particular city. One objective could be to determine the best distribution/allocation of shareable bicycles in various locations within the city. In this example, the measured outcome might be whether a given bicycle in a particular location gets used or not or whether it is used within a predetermined period or with a certain frequency. Another possible measured outcome is the proportion of the time a given bicycle is used compared with the proportion of time it sits unused.

In yet another embodiment, electric bicycles are distributed throughout a city for transportation. The bicycles have to be charged regularly to be useable. The techniques described herein can be used to predict which bicycles should be charged when, based on their characteristics such as location, type of electric bicycle, age, etc. In this example, the bicycles that get charged would be the intervention group (first intervention group), and those that do not get charged would be the control group (second intervention group). The determination of which bicycles to charge and which not to charge can be randomized during the experimental (learning) phase. One goal could be to learn how to predict which bicycles should be charged to maximize their overall usage and to efficiently allocate charging resources.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-3, but the embodiments are not limited to the illustrated structure or application.

The flowcharts and block diagrams in the figures illustrate the architecture, functionality, and operation of possible implementations of systems, methods and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™ Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Generally, "module," as used herein, includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e. open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g. AB, AC, BC or ABC).

Aspects herein can be embodied in other forms without departing from the spirit or essential attributes thereof. Accordingly, reference should be made to the following claims rather than to the foregoing specification, as indicating the scope hereof.

What is claimed is:

1. A system, comprising:

a processor; and a memory storing machine-readable instructions that, when executed by the processor, cause the processor to:

identify, for each unit of a training dataset based on covariates representing characteristics of units, k nearest-neighbor units in each of:

a first group receiving a first intervention; and a second group receiving a second intervention;

calculate, for each unit, a weighted average of the k nearest-neighbor units in each of:

the first group as a first outcome; and the second group as a second outcome;

calculate, for each unit, a difference between the first outcome and the second outcome as an individual intervention effect for that unit;

train directly a machine-learning-based regression model on a relationship between the individual intervention effects and the covariates to enable intervention-effect prediction for units outside the training dataset;

determine, using the machine-learning-based regression model, a specific intervention to which a specific unit outside the training dataset is to be subjected, wherein the specific intervention is either the first intervention or the second intervention; and causing the specific unit to be subjected to the specific intervention.

2. The system of claim 1, wherein the units of the training dataset are one of individual human beings, households, groups of human beings, autonomous machines, and inanimate objects.

3. The system of claim 1, wherein the second intervention is a null intervention and the second group is a control group.

4. The system of claim 1, wherein the machine-learning-based regression model includes one or more of a neural network, a linear regression model, and a decision-tree-based regression model.

5. The system of claim 1, wherein at least one of the first intervention and the second intervention is one of a marketing message, exposure to a product feature, a physical manipulation, an electromagnetic manipulation, and a medical treatment.

6. The system of claim 1, wherein the machine-readable instructions include instructions that, when executed by the processor, cause the processor to identify, for each unit of the training dataset, the k nearest-neighbor units in the first group and the k nearest-neighbor units in the second group based on Euclidean distance with respect to the covariates.

7. The system of claim 1, wherein the first intervention and the second intervention are carried out in connection with a randomized experiment.

8. A non-transitory computer-readable medium storing instructions that, when executed by a processor, cause the processor to:

identify, for each unit of a training dataset based on covariates representing characteristics of units, k nearest-neighbor units in each of:

a first group receiving a first intervention; and a second group receiving a second intervention;

calculate, for each unit, a weighted average of the k nearest-neighbor units in each of:

the first group as a first outcome; and the second group as a second outcome;

calculate, for each unit, a difference between the first outcome and the second outcome as an individual intervention effect for that unit;

train directly a machine-learning-based regression model on a relationship between the individual intervention effects and the covariates to enable intervention-effect prediction for units outside the training dataset;

determine, using the machine-learning-based regression model, a specific intervention to which a specific unit outside the training dataset is to be subjected, wherein the specific intervention is either the first intervention or the second intervention; and causing the specific unit to be subjected to the specific intervention.

9. The non-transitory computer-readable medium of claim 8, wherein the second intervention is a null intervention and the second group is a control group.

10. The non-transitory computer-readable medium of claim 8, wherein the first intervention and the second intervention are part of a randomized experiment.

11. A method comprising:

identifying, by a processor for each unit of a training dataset based on covariates representing characteristics of units, k nearest-neighbor units in each of:

a first group receiving a first intervention; and a second group receiving a second intervention;

calculating, by the processor for each unit, a weighted average of the k nearest-neighbor units in each of:

the first group as a first outcome; and the second group as a second outcome;

calculating, by the processor for each unit, a difference between the first outcome and the second outcome as an individual intervention effect for that unit;

training directly, by the processor, a machine-learning-based regression model on a relationship between the individual intervention effects and the covariates to enable intervention-effect prediction for units outside the training dataset;

determining, by the processor operating the machine-learning-based regression model, a specific intervention to which a specific unit outside the training dataset is to be subjected, wherein the specific intervention is either the first intervention or the second intervention; and causing the specific unit to be subjected to the specific intervention.

12. The method of claim 11, wherein the units of the training dataset are one of individual human beings, households, groups of human beings, autonomous machines, and inanimate objects.

13. The method of claim 11, wherein the second intervention is a null intervention and the second group is a control group.

14. The method of claim 11, wherein the machine-learning-based regression model includes one or more of a neural network, a linear regression model, and a decision-tree-based regression model.

15. The method of claim 11, wherein at least one of the first intervention and the second intervention is one of a marketing message, exposure to a product feature, a physical manipulation, an electromagnetic manipulation, and a medical treatment.

16. The method of claim 11, further comprising causing, via the processor, the specific intervention to be administered to the specific unit.

17. The method of claim 11, wherein identifying, for each unit of the training dataset, the k nearest-neighbor units in the first group and the k nearest-neighbor units in the second group is based on Euclidean distance with respect to the covariates.

18. The method of claim 11, wherein the first intervention and the second intervention are carried out in connection with a randomized experiment.

* * * * *